(12) United States Patent
Ratledge et al.

(10) Patent No.: US 7,674,609 B2
(45) Date of Patent: Mar. 9, 2010

(54) **CULTURE OF *CRYPTHECODINIUM COHNII* AND MICROORGANISMS DERIVED THEREFROM**

(75) Inventors: Colin Ratledge, Beverley (GB); Alistair James Anderson, Hull (GB); Kanagasooriyam Kanagachandran, Dehiwala (LK)

(73) Assignee: The University of Hull, Hull, North Humberside (GB)

( * ) Notice: Subject to any disclaimer, the term of this patent is extended or adjusted under 35 U.S.C. 154(b) by 321 days.

(21) Appl. No.: 10/467,003

(22) PCT Filed: Feb. 4, 2002

(86) PCT No.: PCT/GB02/00495

§ 371 (c)(1),
(2), (4) Date: Aug. 1, 2003

(87) PCT Pub. No.: WO02/064751

PCT Pub. Date: Aug. 22, 2002

(65) Prior Publication Data

US 2004/0072330 A1    Apr. 15, 2004

(30) Foreign Application Priority Data

Feb. 9, 2001   (GB) ................................ 0103301.8

(51) Int. Cl.
*C12P 7/64* (2006.01)
(52) U.S. Cl. .................. 435/134; 435/254.1; 435/244
(58) Field of Classification Search ........................ None
See application file for complete search history.

(56) References Cited

U.S. PATENT DOCUMENTS

| | | | |
|---|---|---|---|
| 3,444,647 | A | 5/1969 | Takahashi |
| 5,130,242 | A | 7/1992 | Barclay |
| 5,130,244 | A | 7/1992 | Nishimaki et al. |
| 5,244,921 | A | 9/1993 | Kyle et al. |
| 5,374,657 | A | 12/1994 | Kyle |
| 5,397,591 | A | 3/1995 | Kyle et al. |
| 5,407,957 | A | 4/1995 | Kyle et al. |
| 5,429,942 | A | 7/1995 | Kock et al. |
| 5,492,938 | A | 2/1996 | Kyle et al. |
| 5,550,156 | A | 8/1996 | Kyle |
| 5,567,732 | A | 10/1996 | Kyle et al. |
| 5,658,767 | A | 8/1997 | Kyle |
| 5,711,983 | A | 1/1998 | Kyle et al. |
| 6,946,248 | B2 * | 9/2005 | Sowers et al. .................. 435/6 |

FOREIGN PATENT DOCUMENTS

| | | |
|---|---|---|
| EP | 0 515 460 | 12/1992 |
| JP | 63-12288 | 1/1988 |
| JP | 6-113868 | 4/1994 |
| JP | 7-87988 | 4/1995 |
| WO | WO 89/00606 | 1/1989 |
| WO | WO 96/40106 | 12/1996 |
| WO | WO 99/06585 | 2/1999 |
| WO | WO 00/54575 | 9/2000 |
| WO | WO 01/04338 | 1/2001 |
| WO | WO 01/49282 | 7/2001 |

OTHER PUBLICATIONS

Wery et al. International Journal of Systematic and Evolutionary Microbiology (2001), 51, 1789-1796.*
Himes et al.; "Genetic analysis in the dinoflagellate *Crypthecodinium* (*Gyrodinium*) *cohnii*: Evidence for unusual meiosis"; *Proc. Nat. Acad. Sci. USA*; (Nov. 1975); vol. 72, No. 11.; pp. 4546-4549.
U.S. Appl. No. 10/030,700, Ratledge et al.
U.S. Appl. No. 11/183,831, Ratledge et al.
Meyer A et al., Biosnythesis of Docosahexaenoic Acid in *Euglena gracilis*: Biochemical and Molecular Evidence for the Involvement of a Delta-4 Fatty Acyl Group Desaturase, Biochemistry42(32):9779-88.
Bahnweg: "Studies on the Physiology of Thraustochytriales, II. Carbon Nutrition of *Thraustochytrium* spp., *Schizochytrium* sp., *Japanochytrium* sp., *Ulkenia* spp., and *Labryinthuloides* spp."; Veroff. Inst. Meeresforsch.Bremerh;(1979); 17:pp. 269-273.
Bajpai et al.; "Production of Docosahexaenoic Acid by *Thraustochytrium aureum*"; Applied Microbiology and Biotechnology; (1991); 35:pp. 706-710.
Buckmaster, A. (http:www.mtsu.edu/~mcnair/abstracts/abuckmaster02.pdf)(summer 2002).
Klein Breteler, WCM et al. (1999) Trophic upgrading of food quality by protozoans enhancing copepod growth: Marine Biology, 135(1):191-198.
Beach et al.; Biosynthesis of Oleic Acid and Docosahexaenoic Acid by a Heterotrophic Marine Dinoflagellate *Crypthecodinium cohnii*; Biochimica et Biophysica Acta; (1974): 369:pp. 16-24.

(Continued)

*Primary Examiner*—Irene Marx
(74) *Attorney, Agent, or Firm*—Leydig, Voit & Mayer, Ltd.

(57) ABSTRACT

*Crypthecodinium cohnii*, or microorganisms derived from *Crypthecodinium cohnii*, are grown in a culture medium including propionic acid. The propionic acid increases the production of one or more of dry cell weight, total lipid and docosahexaenoic acid.

12 Claims, 2 Drawing Sheets

OTHER PUBLICATIONS

Droop; "Algal Physiology and Biochemistry, Chapter 19: Heterotrophy of Carbon"; University of California Press; (1974); vol. 10; pp. 530-559.

Gold et al.; "Growth Requirements of *Gyrodinium cohnii*"; J. Protozool.; (1966); vol. 13, No. 2; pp. 255-257.

Hastings et al.; "Qualitative Requirements and Utilization of Nutrients: Algae"; Handbook Series in Nutrition and Food, Section D: Nutritional Requirements, CRC Press, Cleveland, Ohio; (1977); vol. 1; pp. 87-163.

Henderson et al.; "Lipid Composition and Biosynthesis in the Marine Dinoflagellate *Crypthecodinium cohnii*"; Phytochemistry; (1988); vol. 27, No. 6; pp. 1679-1683.

Henderson et al.; "Polyunsaturated Fatty Acid Metabolism in the Marine Dinoflagellate *Crypthecodinium cohnii*"; Biochemistry; (1991); vol. 30, No. 6; pp. 1781-1787.

Provasoli; "Marine Ecology, 5. Cultivation of Animals"; John Wiley & Sons; (1977); vol. 3; pp. 1295-1319.

Provasoli et al.; "Nutrition of the American Strain of *Gyrodinium cohnii*"; Archiv fur Mikrobiologie; 42; pp. 196-203, 1962.

Brands, S.J. (comp.); 1989-2004; *Systema Naturae 2000*. Amsterdam, The Netherlands.

Lloyd, D., et al.; "Propionate Assimilation in the Flagellate *Polytomella caeca*"; Biochem. J; (1968); vol. 109; pp. 897-907.

Smith et al.; "Metabolism of Propionate by Sensitive and Resistant Strains of Blue-Green Algae"; Biochemical Society Transactions; 537th Meeting, Canterbury, (1973); vol. 1 pp. 707-709.

Brands, S.J. (comp.); 1989-2004; *Systema Naturae 2000*. Amsterdam, The Netherlands.

Hastings et al.; "Qualitative Requirements and Utilization of Nutrients: Algae"; *CRC Press; Handbook Series in Nutrition and Food, Section D: Nutritional Requirements*; (1977); vol. 1; pp. 87-163.

Lloyd et al.; "Propionate Assimilation in the Flagellate *Polytomella caeca*"; Biochem. J.; (1968); vol. 109; pp. 897-907.

Provasoli et al.; "Nutrition of the American Strain of *Gyrodinium cohnii*"; *Archive für Mikrobiologic*; (1962); vol. 42; pp. 196-203.

Smith et al.; "Metabolism of Propionate by Sensitive and Resistant Strains of Blue-Green Algae"; *Biochemical Society Transactions; 537th Meeting, Canterbury*; (1973); vol. 1, pp. 707-709.

Shield® brand NA Liquid Mold Inhibitor, http://www.graintreatment.com/technicaldocuments/section_2_article2.pdf, printed on Jul. 18, 2007.

"Sodium propionate," http://en.wikipedia.org/wiki/Sodium_propionate; printed on Jul. 18, 2007.

"Sodium Propionate: Crops," National Organic Standards Board Technical Advisory Panel Review, 2002, www.ams.usda.gov/NOP/NationalList/TAPReviews/SodPropionate.pdf, lines 56-66.

P. 1, Seventeenth Report of the Joint FAO/WHO Expert Committee on Food Additives, *Wld Hlth Org. techn. Rep. Ser.*, 1974, No. 539; *FAO Nutrition Meetings Report Series*, 1974, No. 53; http://www.inchem.org/documents/jecfa/jecmono/v05je16.htm; printed on Jul. 18, 2007.

Vazhappilly et al., "Eicosapentaenoic Acid and Docosahexaenoic Acid Production Potential of Microalgae and their Heterotrophic Growth", Journal of the American Oil Chemists, 75, No. 3, pp. 393-397 (1998).

Du Preez et al., "Production of Gamma-Linolenic Acid by *Mucor circinelloides* and *Mucor rouxii* with Acetic Acid as Carbon Substrate", Biotechnology Letters, 17, No. 9, pp. 933-938 (1995).

Vazhappilly et al., "Heterotrophic Production Potential of Omega-3 Polyunsaturated Fatty Acids by Microalgae and Algae-like Microorganisms", Botanica Marina, 41, pp. 553-558 (1998).

Pringsheim, E.G., "Micro-Organisms From Decaying Seaweed", Nature, 178, pp. 480-481 (1956).

Henderson et al., "Polyunsaturated Fatty Acid Metabolism in the Marine Dinoflagellate *Crypthecodinium cohnii*", Phytochemistry, 30, No. 6, pp. 1781-1787 (1991).

Sowers et al., "Growth of Acetotrophic, Methane-producing Bacteria in a pH Auxostat", Current Microbiology, 11, pp. 227-230 (1984).

A. G. Callely et al.; "The Metabolism of Propionate in the Colourless alga, *Prototheca zopfii*"; Biochem. Journal (1964), vol. 92, pp. 338-345.

Tuttle et al., "An optimal growth medium for the dinoflagellate *Crypthecodinium cohnii*", Phycologia, Blackwell Scientific Publ., 14:1, 1-8 (1975).

Martin et al., "A Method for the Regulation of Microbial Population Density during Continuous Culture at High Growth Rates", Arch. Microbiol., 107, pp. 41-47 (1976).

Shahidi et al., "Omega-3 Fatty Acid Concentrates: Nutritional Aspects and Production Technologies", Trends in Food Science & Technology, 9, pp. 230-240 (1998).

Oltmann et al., "Modification of the pH-Auxostat Culture Method for the Mass Cultivation of Bacteria", Biotechnology and Bioengineering. vol. XX, pp. 921-925 (1978).

Provasoli et al., "Some Nutritional Characteristics of *Gyrodinium cohnii*, a Colorless Marine Dionflagellate", Journal of Photozoology, vol. 4, Supplement, p. 7 (1957).

du Preez et al., "The Utilization of Short-Chain Monocarboxylic Acids as Carbon Sources for the Production of Gamma-Linolenic Acid by *Mucor* Strains in Fed-batch Culture", World Journal of Microbiology & Biotechnology, vol. 12, pp. 68-72, (1996).

* cited by examiner

CULTURE OF *CRYPTHECODINIUM COHNII* AND MICROORGANISMS DERIVED THEREFROM

The invention relates to a method for culture of a microorganism selected from the group consisting of *Crypthecodinium cohnii* and microorganisms derived from *Crypthecodinium cohnii*. Additionally, the invention relates to a medium for the culture of such a microorganism.

U.S. Pat. No. 5,407,957 discloses a method for culture of *Crypthecodinium cohnii* in a medium comprising glucose, as a carbon source, and yeast extract, dissolved in sea-water. WO 01/04338 discloses a method for culture of *Crypthecodinium cohnii* in a medium comprising acetic acid/acetate, as a carbon source, yeast extract and sea salt. In both of these methods, the *Crypthecodinium cohnii* produce docosahexaenoic acid which can be extracted from the culture. Other uses for cultures of *Crypthecodinium cohnii* can also be envisaged.

According to a first aspect of the invention, there is provided a method for culture of a microorganism selected from the group consisting of *Crypthecodinium cohnii* and microorganisms derived from *Crypthecodinium cohnii*, comprising culturing the microorganism in a medium containing propionic acid. Preferably, the medium also contains a compound that is the main carbon source for the microorganism during the culture.

According to a second aspect of the invention, there is provided a method for culture of a microorganism selected from the group consisting of *Crypthecodinium cohnii* and microorganisms derived from *Crypthecodinium cohnii*, comprising culturing the microorganism in a medium containing a carbon source and an acid, the acid causing an increase in the ratio of "cyst" to "swimmer" forms of the microorganism.

According to a third aspect of the invention, there is provided a medium for culture of *Crypthecodinium cohnii*, or a microorganism derived therefrom, the medium containing natural or artificial sea salt and propionic acid. Preferably, the medium also contains a compound that is the main carbon source for the microorganism during the culture.

The following is a more detailed description, by way of example, of embodiments of the invention, reference being made to the appended drawings in which.

EXAMPLE 1

Figure 2:
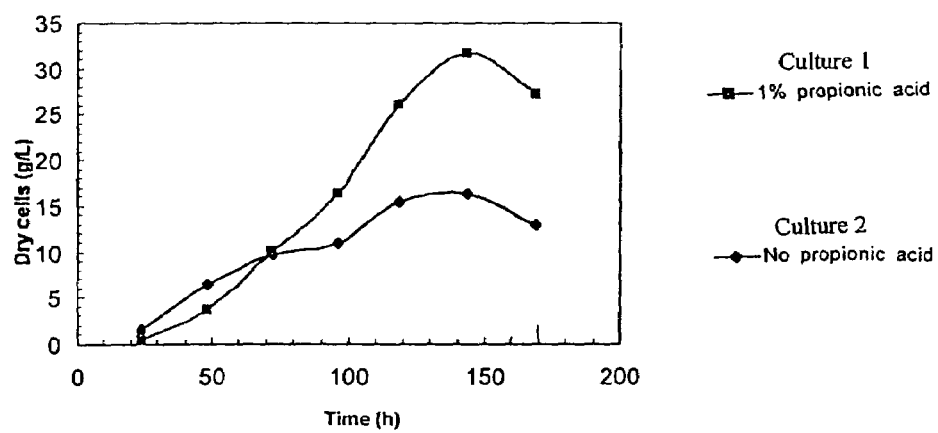
FIG. 2 is a graph showing dry cell weight per volume of culture over time for first and second cultures of *Crypthecodinium cohnii*.

This Example consists of the first and second cultures depicted in FIG. 2 and demonstrates the effect of a relatively small amount of propionic acid in a culture medium, on the culture of *Crypthecodinium cohnii* with acetic acid/acetate as a main carbon source.

The growth medium used for the first culture contained (initially) propionic acid (1% v/v), sodium acetate (8 g/L), yeast extract (7.5 g/L) and sea salts (25 g/L). The growth medium used for the second culture was the same but with the propionic acid omitted. Before use, the pH of each growth medium was adjusted to 6.5 by the addition of NaOH and the medium was then autoclaved at 121° C. for 1 hour.

The first and second cultures used the strain of *Crypthecodinium cohnii* available from the American Type Culture Collection and identified by the number 30772 (*C. cohnii* ATCC 30772).

Figure 1:
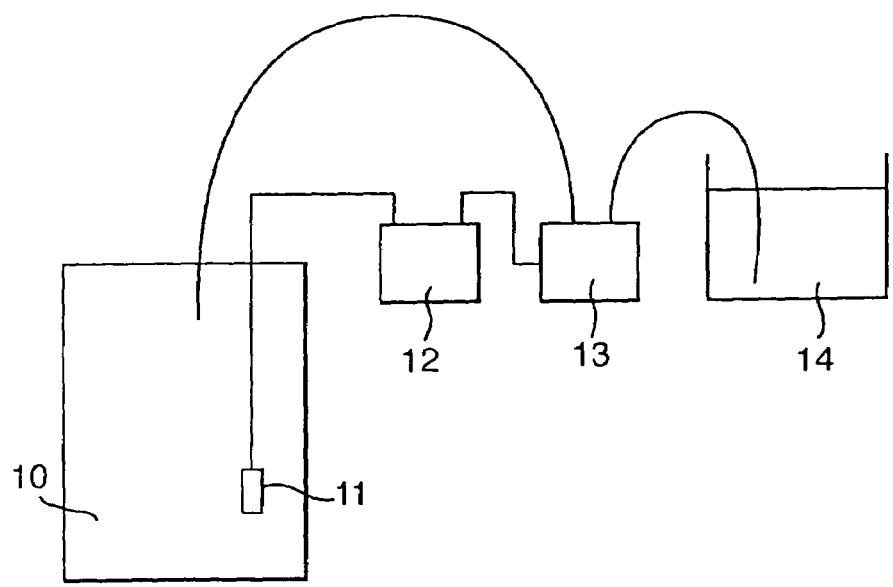
FIG. 1 is a schematic representation of part of a fermentation apparatus.

Each culture was performed, separately, in a fermentation apparatus that is shown in FIG. 1. The apparatus included a 5 L fermenter 10 of known type. The fermenter 10 was provided with a pH electrode 11 that was positioned in the fermenter 10 for monitoring the pH of the growth medium in the fermenter 10. The pH electrode 11 was connected via a control device 12 to a pump 13. The control device 12 was programmed to cause the pump 13 to pump acetic acid (50% v/v) from a reservoir 14 into the fermenter 10 when the pH electrode 11 detected a pH greater than a predetermined value (in this case pH 6.5 for both the first and second cultures).

If, during the culture, the pH fell below 6.5, the pH was brought back to 6.5 by adding KOH (2M). This was done automatically.

The fermenter 10 was also provided with a thermometer (not shown) and a heater (not shown) arranged to maintain the growth medium (and the *C. cohnii* 30772) at a desired temperature within the fermenter 10 (in this case 27° C. for both the first and second cultures).

The fermenter 10 was also provided with an aerator (not shown) that was connected to a source of air (not shown) for aerating the growth medium within the fermenter 10. An oxygen sensor (not shown) was positioned for measuring dissolved oxygen concentration in the growth medium within the fermenter 10. A stirrer (not shown) was provided for stirring the growth medium (and the *C. cohnii* 30772). The oxygen sensor was connected to the stirrer by a control device (not shown) for varying the speed of the stirrer in response to the oxygen concentration detected by the oxygen sensor so as to maintain the oxygen concentration at a desired level. For both the first and second cultures the aerator was set to aerate the culture at a rate of 1 volume of air per volume of culture per minute. The control device connected to the oxygen sensor and the stirrer was set so that the dissolved oxygen concentration was maintained above 30% of air saturation (the initial stirrer speed being 300 rpm).

To start each culture, 3.5 L of the appropriate growth medium was added to the fermenter 10. An inoculum of *C. cohnii* 30772 in 880 ml medium containing acetic acid/acetate, yeast extract and sea salt was then added to the fermenter (the preparation of the inoculum is described below). The fermenter 10 was then closed and the culture was heated to the desired operating temperature, aerated and stirred as described above.

In both the first and second cultures, the control device 12 caused the pump 13 to pump acetic acid into the fermenter 10 so as to maintain the pH at 6.5. This process, sometimes referred to as pH-stat operation, is described in detail in WO 01/04338. Briefly, it is believed that the *Crypthecodinium cohnii* metabolises the acetate in the growth medium (either in the form of acetate or acetic acid) as a carbon source. The utilisation of the acetate increases the pH and this triggers the control device 12 to cause acetic acid to be pumped into the fermenter. The added acetic acid initially reduces the pH but is eventually metabolised itself by the *Crypthecodinium cohnii* (either as acetic acid or acetate) thereby causing the pH to rise again. In turn more acetic acid is added and this process continues until growth stops or the culture is terminated. Over the course of the culture, the amount of acetic acid used is many times the initial content of acetate and so this method allows large quantities of acetic acid to be given as a carbon source while the concentration of acetic acid/acetate in the medium is maintained at levels sufficiently low not to be significantly detrimental to growth.

The yeast extract present in the growth medium is provided, primarily, as a source of nitrogen, essential vitamins, amino acids and growth factors. The sea salts are needed for osmo-protection of the C. cohnii 30772, which are marine cells in origin.

During the first and second cultures, samples of the cultures were taken at time intervals. Each sample was analysed to determine dry cell weight. After 170 hours, the first and second cultures were stopped.

Dry cell weight measurements of the cultures of C. cohnii 30772 are shown in FIG. 2. It is clear that the presence of propionic acid greatly increased the growth of the C. cohnii 30772 such that, towards the later stages of the cultures, dry cell weight in the first culture (with propionic acid) was approximately double that of the second culture (without propionic acid).

In the first culture (with propionic acid), the cellular lipid content was about 55-65% of the dry cell weight and the content of docosahexaenoic acid was about 35-40% of the total lipid. In the second culture (without propionic acid), the cellular lipid content was about 40% of the dry cell weight and the content of docosahexaenoic acid was about 40% of the total lipid. The amount of DHA produced in the first culture (that is to say the overall amount of DHA produced— not DHA per dry cell weight), was about 6-8 g/L compared to about 2-3 g/L in the second culture.

Hence, it is clear that the propionic acid increased the amount of docosahexaenoic acid, total lipid, and dry cell weight, produced in the first culture, compared to a culture in which an identical microorganism was grown in a medium that was identical other than for the omission of propionic acid, under identical conditions of pH, temperature and aeration.

The production of increased amounts of docosahexaenoic acid is clearly advantageous as this fatty acid is a useful food supplement. The production of increased amounts of total lipid, or dry cell mass, is also advantageous, per se. For example, harvested Crypthecodinium cohnii may, independently of its docosahexaenoic content, be used as a foodstuff, particularly for animals including fish and developing fish or other marine animals.

Additionally microscopic observations of the first and second-cultures were made over the course of the cultures. Crypthecodinium cohnii exists in two forms, a non-motile form known as "cysts" and a motile form known as "swimmers". In the first culture, with propionic acid, only non-motile cysts were present after 24 hours. These cysts were dividing into 2 or 4 cysts. In the second culture, a mixture of non-motile cysts and motile swimmers was present up to 140 hours and the cysts were giving rise to swimmers.

While not limiting the invention to any particular mechanism, it is thought that the increased production of docosahexaenoic acid, total lipid and dry cell weight, is due to the propionic acid arresting the conversion of the cyst form of Crypthecodinium cohnii to the swimmer form. The non-motile cysts are believed to accumulate greater levels of lipid, including docosahexaenoic acid, than the swimmer form of the organism. Moreover, the cysts do not expend energy in "swimming". Hence it is believed that a greater proportion of carbon from the acetic acid is converted to fatty acid material, including docosahexaenoic acid.

Preparation of Inocula

Example 1

The inoculum for the first culture was prepared as follows.

Cells of Crypthecodinium cohnii ATCC 30772 were grown at 27° C. for 4 to 5 days in a screw-capped tube (25 mL) containing 5 mL of glucose/salts medium (ATCC 460) and used to inoculate a starter culture. This starter culture was grown at 27° C. for 4 days in a static flask (250 mL) containing 100 mL medium containing (per liter): glucose (9 g), yeast extract (2 g) and sea salts (25 g). A shake-flask culture was grown in a flask (250 mL) containing 100 mL medium composed of (per liter): glucose (27 g), yeast extract (3.8 g), sea salts (25 g) and propionic acid (10 mL). This culture was inoculated (10% v/v) with the static culture and grown at 27° C. for 3 days with shaking. A small pH-stat culture was grown in a fermenter (1 L) containing 800 mL of medium composed of (per liter): sodium acetate (8 g), yeast extract (7.5 g), sea salts (25 g) and propionic acid (10 mL). The pH of the medium was adjusted to approximately 6.5 with NaOH, prior to autoclaving for 60 minutes at 121° C. The pH-stat culture was inoculated (10% v/v) with the culture grown in the shake-flask on the medium containing glucose and propionic acid, as described above. The pH was maintained at 6.5 by the automatic addition of acetic acid (50% v/v) and KOH (2 M) and the temperature was maintained at 27° C. The culture was stirred at 300-1000 rpm and aerated at 0.2 to 1.0 vol air per vol medium per min (vvm), increasing the stirring speed and aeration as necessary to maintain a dissolved oxygen concentration above 30% of air saturation.

The inoculum for the second culture was prepared as per that of the first culture but the propionic acid was omitted from the shake-flask and the small pH-stat cultures.

In each case, the complete contents (about 880 ml) of the small pH-stat culture was added, after 3 days, as the inoculum to the 5 L fermenter 10, so as to start the first and second cultures (as described above).

Example 2

Figure 3:
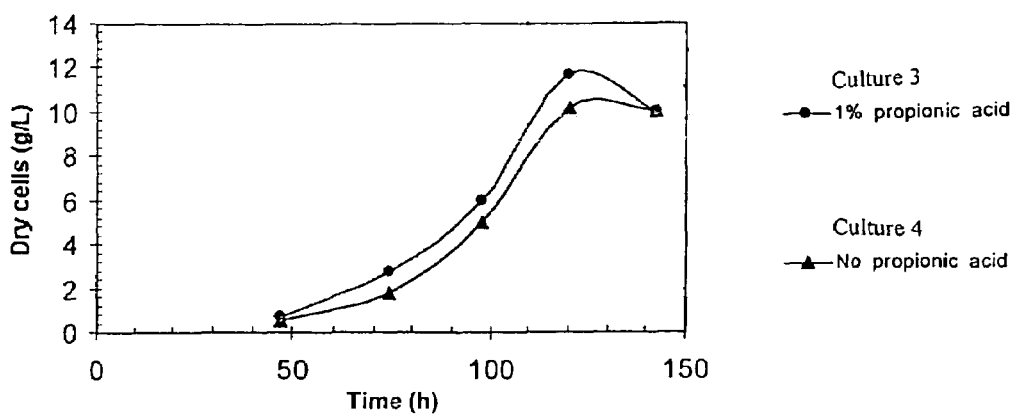
FIG. 3 is a graph showing dry cell weight per volume of culture over time for third and fourth cultures of *Crypthecodinium cohnii*.
Figure 4:
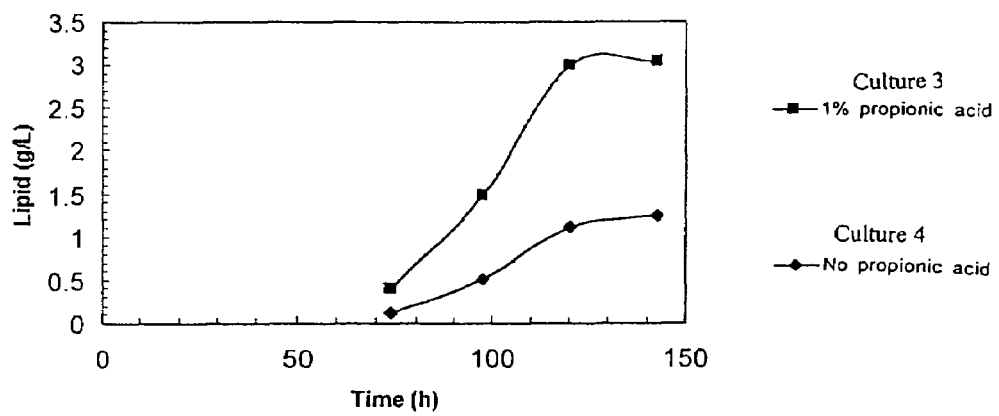
FIG. 4 is a graph showing lipid production per volume of culture over time for the third and fourth cultures.
Figure 5:
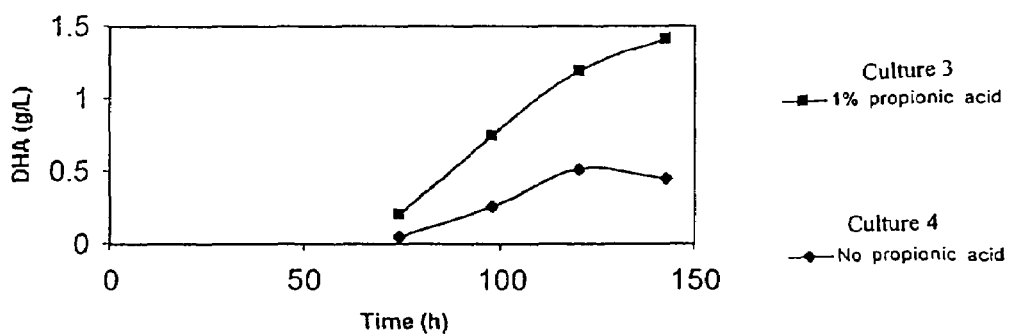
FIG. 5 is a graph showing docosahexaenoic acid (DHA) production per volume of culture over time for the third and fourth cultures.

This Example consists of the third and fourth cultures, depicted in FIGS. 3 to 5, and demonstrates the effect of a relatively small amount of propionic acid in a culture medium, on the culture of Crypthecodinium cohnii with glucose as the main carbon source.

The growth medium used for the third culture contained (initially) propionic acid (1% v/v), glucose (60 g/L—autoclaved separately), yeast extract (7.5 g/L) and sea salts (25 g). The growth medium used for the fourth culture was the same but with the propionic acid omitted. In each case, the pH was 6.5.

The microorganism used was Crypthecodinium cohnii 30772.

For each of the third and fourth cultures, the Crypthecodinium cohnii was grown in a 5 L fermenter. The cultures were initiated by inoculating 3.5 L of the appropriate growth medium with 350 ml of a 3 day old shaking-flask culture of Crypthecodinium cohnii. The inoculum for the third culture was prepared using the same growth medium as that used in the third culture (i.e., with propionic acid) and the inoculum for the fourth culture was prepared using the same growth medium as that used in the fourth culture (i.e., without propionic acid).

Cultures were aerated at 1 volume of air per volume of culture per minute and the dissolved oxygen concentration was maintained above 30% of air saturation by increasing the stirrer speed as required, from an initial speed of 300 rpm. The growth temperature was 27° C. and the pH was maintained at 6.5 by addition of KOH (2 M) and $H_2SO_4$ (1 M).

The effects of the propionic acid are shown in FIGS. 3 to 5. FIG. 3 shows that the dry cell weight produced in the third culture (with propionic acid) was about 20% greater, towards the later stages of the culture, than that produced in the fourth culture (without propionic acid). FIG. 4 shows that the amount of total lipid produced in the third culture was greater than twice that produced in the fourth culture. FIG. 5 shows that the amount of docosahexaenoic acid produced in the third culture was greater than twice that produced in the fourth culture.

Hence, propionic acid increased the production of dry cell weight and, more markedly, total lipid and docosahexaenoic acid.

Example 3

The value of including propionic acid in the culture medium was also shown with another strain of *Crypthecodinium cohnii* (ATCC 30541). This strain was grown on acetic acid in pH-stat fermenters as described in Example 1 with and without the inclusion of propionic acid at 1% of the volume of the initial culture medium. The results are shown in Table 1 below.

TABLE 1

Performance of *Crypthecodinium cohnii* 30541 grown in acetic acid pH-stat fermenters with the culture medium as given in Example 1, with and without the inclusion of propionic acid in the culture medium at 1%. Analytical data refer to samples taken from the fermenters after 140-150 hours growth.

| Culture | Cell dry wt (g/l) | Lipid in cells (% w/w) | DHA in lipid (% w/w) | Total DHA produced (g/litre) |
|---|---|---|---|---|
| + propionate | 75 | 20 | 33 | 5 |
| − propionate | 46 | 18 | 33 | 2.7 |

As seen in Table 1, the inclusion of 1% propionic acid increased the amount of docosahexaenoic acid produced in the culture by about 85% and increased the dry cell weight produced in the culture by over 60%.

Hence, the Examples show that propionic acid can increase dry cell weight, lipid and docosahexaenoic production in cultures of *Crypthecodinium cohnii* grown with either acetic acid or glucose as a principal carbon source. It is believed that propionic acid might similarly increase one or more of dry cell weight, lipid or docosahexaenoic acid when other carbon sources are used. It is also possible to grow *Crypthecodinium cohnii* with propionic acid itself as the sole or major carbon source.

Once in aqueous solution, propionic acid will dissociate to give the propionate ion ($CH_3CH_2COO^-$) in equilibrium with the protonated form itself ($CH_3CH_2COOH$). It is not known whether it is the protonated form, the propionate ion or both species that have the observed effect on *Crypthecodinium cohnii*. For the purposes of this specification, the term propionic acid, when referring to aqueous solutions, is used to refer to either or both of the protonated form ($CH_3CH_2COOH$) and the propionate ion ($CH_3CH_2COO^-$).

Other strains of *Crypthecodinium cohnii* may also be used. Additionally, propionic acid may have advantageous effects on the growth of microorganisms derived from *Crypthecodinium cohnii*.

Whereas the Examples use 1% (v/v) propionic acid other concentrations can be used. Preferably the concentration is from about 0.25% (v/v) to about 2% (v/v), more preferably from about 0.5% (v/v) to about 1.5% (v/v).

In Examples 1 and 2, the propionic acid was gradually consumed during the cultures.

Accordingly, additional propionic acid may be beneficially added during the course of culture. Preferably, propionic acid may be added so as to maintain a desired concentration in the medium.

Other acids, particularly other carboxylic acids, may demonstrate the same beneficial effect as propionic acid.

The invention claimed is:

1. A method for culturing *Crypthecodinium cohnii*, comprising
   culturing a strain of *Crypthecodinium cohnii* in a medium containing 60 g/L glucose or 8 g/L of acetate/acetic acid, 7.5 g/L yeast extracts, 25 g/L natural or artificial sea salts, and 1% (v/v) propionic acid,
   maintaining the culture at a pH of 6.5;
   maintaining the culture at a temperature of 27° C.; and
   aerating the culture at 1 volume of air per volume of culture per minute;
   wherein the propionic acid increases the amount of docosahexaenoic acid produced in the culture compared to a comparison culture in which the same strain of *Crypthecodinium cohnii* is grown in a medium containing 60 g/L glucose or 8 g/L sodium acetate, 7.5 g/L yeast extracts, and 25 g/L natural or artificial sea salts, wherein the comparison culture does not include propionic acid and is maintained at a pH of 6.5, a temperature of 27° C., and is aerated at 1 volume of air per volume of culture per minute.

2. The method according to claim 1, wherein the propionic acid further increases the dry cell weight produced in the culture compared to the comparison culture.

3. The method according to claim 1, wherein the strain of *Crypthecodinium cohnii* is *Crypthecodinium cohnii* ATCC 30541.

4. The method according to claim 1, wherein the strain of *Crypthecodinium cohnii* is *Crypthecodinium cohnii* ATCC 30772.

5. The method according to claim 3, wherein the medium contains the 8 g/L acetate/acetic acid and the inclusion of propionic acid increases the amount of docosahexaenoic acid produced in the culture by about 85% compared to the comparison culture.

6. The method according to claim 3, wherein the medium contains the 8 g/L acetate/acetic acid and the inclusion of propionic acid increases the dry cell weight produced in the culture by over 60% compared to the comparison culture.

7. A method for culturing *Crypthecodinium cohnii*, comprising
   culturing a strain of *Crypthecodinium cohnii* in a medium containing 60 g/L glucose or 8 g/L of acetate/acetic acid, 7.5 g/L yeast extracts, 25 g/L natural or artificial sea salts, and 1% (v/v) propionic acid,
   maintaining the culture at a pH of 6.5;
   maintaining the culture at a temperature of 27° C.; and
   aerating the culture at 1 volume of air per volume of culture per minute;
   wherein the propionic acid increases the amount of lipid produced in the culture compared to a comparison culture in which the same strain of *Crypthecodinium cohnii* is grown in a medium containing 60 g/L glucose or 8 g/L sodium acetate, 7.5 g/L yeast extracts, and 25 g/L natural or artificial sea salts, wherein the comparison culture does not include propionic acid and is maintained at a pH of 6.5, a temperature of 27° C., and is aerated at 1 volume of air per volume of culture per minute.

8. The method according to claim 7, wherein the propionic acid further increases the dry cell weight produced in the culture compared to the comparison culture.

9. The method according to claim 7, wherein the strain of *Crypthecodinium cohnii* is *Crypthecodinium cohnii* ATCC 30541.

10. The method according to claim 7, wherein the strain of *Crypthecodinium cohnii* is *Crypthecodinium cohnii* ATCC 30772.

11. The method according to claim 9, wherein the medium contains the 8 g/L acetate/acetic acid and the inclusion of propionic acid increases the amount of docosahexaenoic acid produced in the culture by about 85% compared to the comparison culture.

12. The method according to claim 9, wherein the medium contains the 8 g/L acetate/acetic acid and the inclusion of propionic acid increases the dry cell weight produced in the culture by over 60% compared to the comparison culture.

* * * * *